(12) United States Patent
Syoda et al.

(10) Patent No.: US 7,041,486 B1
(45) Date of Patent: May 9, 2006

(54) ENZYME HAVING DECOLORIZING ACTIVITY AND METHOD FOR DECOLORIZING DYES BY USING THE SAME

(75) Inventors: Makoto Syoda, Yokohama (JP); Yasushi Sugano, Yokohama (JP); Hidetoshi Kubota, Sakado (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 0 days.

(21) Appl. No.: 09/926,084

(22) PCT Filed: Feb. 25, 2000

(86) PCT No.: PCT/JP00/01093
§ 371 (c)(1),
(2), (4) Date: Aug. 27, 2001

(87) PCT Pub. No.: WO00/50582
PCT Pub. Date: Aug. 31, 2000

(30) Foreign Application Priority Data
Feb. 26, 1999 (JP) .......................... 11-050562

(51) Int. Cl.
*C12N 9/08* (2006.01)
*C12N 1/20* (2006.01)
*C12P 21/06* (2006.01)
*C12Q 1/28* (2006.01)
*C07H 21/04* (2006.01)

(52) U.S. Cl. ............................ 435/192; 435/28; 435/4; 435/69.1; 435/71.1; 435/252.3; 435/320.1; 435/252.33; 536/23.2

(58) Field of Classification Search ................ 435/192, 435/28, 4, 69.1, 71.1, 252.3, 320.1, 252.33, 435/189, 18, 188, 198; 536/23.2; 43/252.3; 8/44.15, 401; 510/392, 393

See application file for complete search history.

(56) References Cited

U.S. PATENT DOCUMENTS 5,976,855 A * 11/1999 Svendsen et al. ........... 435/198

OTHER PUBLICATIONS

Sequence Search Results.*
Seong Jun Kim et al. Characteristics of a Newly Isolated Fungus, *Geotrichum candidum* Dec. 1, Which Decolorizes Various Dy Journal of Fermentation and Bioengineering, vol. 79, No. 6, pp. 601–607, Feb. 23, 1995.*
Seong Jun Kim et al. Purification and Characterization of a Novel Peroxidase from *Geotrichum candidum* Dec. 1 Involved in Decolorization of Dyes Applied and Environmental Microbiology, vol. 65, pp. 1029–1035 Mar., 1999.*

(Continued)

*Primary Examiner*—Manjunath Rao
*Assistant Examiner*—Yong Pak
(74) *Attorney, Agent, or Firm*—Oblon, Spivak, McClelland, Maier & Neustadt, P.C.

(57) ABSTRACT

The invention relates to a novel peroxidase enzyme with high dye degradation activity, the genetic information thereof and a method for degrading and decolorizing dye by using the same. The invention enables the degradation and decolorizing of a wide range of dye types in an efficient manner with no occurrence of any problem, such as secondary pollution due to the generation of hazardous byproducts or the discharge of the greenhouse effect gas due to high-level energy consumption.

In accordance with the invention, further, the enzyme can be supplied at a large quantity, on the basis of the genetic information, so the enzyme can be applied to the treatment of wastewater containing dyes and the like, in the fields of staining industry and the like.

9 Claims, 4 Drawing Sheets

OTHER PUBLICATIONS

Seong Jun Kim et al. Decolorization of Molasses and a Dye by a Newly Isolated Strain of the Fungus, *Geotrichum candidum* Dec. 1, Biotechnology and Bioengineering, vol. 62, No. 1, pp. 114–119, Jun. 15, 1998.*

Seong Jun Kim et al. Batch Decolorization of Molasses by Suspended and Immobilized Fungus of *Geotrichum candidum* Dec. 1 Journal of Bioscience and Bioengineering, vol. 88, No. 5, pp. 586–589, Aug. 11, 1999.*

S. J. Kim, et al., Applied and Environmental Microbiology, vol. 65, No. 3, pp. 1029–1035, "Purification and Characterization of a Novel Peroxidase from *Geotrichum Candidum* Dec. 1 Involved in Decolorization of Dyes", Mar. 1999.

S. J. Kim, et al., Biotechnology and Bioengineering, vol. 62, No. 1, pp. 114–119, "Decolorization of Molasses and a Dye by a Newly Isolated Strain of the Fungus *Geotricum Candidum* Dec. 1", Jan. 5, 1999.

S. J. Kim, et al., Journal of Fermentation and Bioenginnering, vol. 79, No. 6, pp. 601–607, "Characteristics of a Newly Isolated Fungus, *Geotrichum Candidum* Dec. 1, Which Decolorizes Various Dyes", 1995.

Y. Sugano, et al., Database EMBL 'Online!', AC: AB013135, pp. 1–2, XP–002217518, "Galactomyces Geotrichum mRNA for DyP Complete CDS", May 10, 1999.

A. Conesa, et al., Journal of Biotechnology, vol. 93, No. 2, pp. 143–158, XP–002217519, "Fungal Peroxidases: Molecular Aspects and Applications", 2002.

* cited by examiner

FIG. 4

|     | 43 | | | | | | | | | | | □ | 55 | | | | 165 | | | | | | | | | | | ● | 177 |
|-----|----|---|---|---|---|---|---|---|---|---|---|---|----|---|---|---|-----|---|---|---|---|---|---|---|---|---|---|---|-----|
| CCP | Gly | Pro | Val | Leu | Val | Arg | Leu | Ala | Trp | His | Thr | Ser | Gly | — | — | — | Arg | Glu | Val | Val | Ala | Leu | Met | Gly | Ala | His | Ala | Leu | Gly |
| | 97 | | | | | | | | | | | | 109 | | | | 258 | | | | | | | | | | | | 270 |
| ECP | Ala | Gly | Leu | Phe | Ile | Arg | Met | Ala | Trp | His | Gly | Ala | Gly | — | — | — | Glu | Thr | Val | Ala | Leu | Ile | Ala | Gly | Gly | His | Thr | Leu | Gly |
| | 47 | | | | | | | | | | | | 59 | | | | 175 | | | | | | | | | | | | 187 |
| ARP | Val | Arg | Lys | Ile | Leu | Arg | Ile | Val | Phe | His | Asp | Ala | Ile | — | — | — | Asp | Glu | Val | Val | Asp | Leu | Leu | Ala | Ala | His | Ser | Leu | Ala |
| | 37 | | | | | | | | | | | | 49 | | | | 164 | | | | | | | | | | | | 176 |
| MnP | Ala | His | Glu | Val | Ile | Arg | Leu | Thr | Phe | His | Asp | Ala | Ile | — | — | — | Phe | Glu | Val | Val | Ser | Leu | Leu | Ala | Ser | His | Thr | Val | Ala |
| | 38 | | | | | | | | | | | | 50 | | | | 167 | | | | | | | | | | | | 179 |
| LiP | Ala | His | Glu | Ser | Ile | Arg | Leu | Val | Phe | His | Asp | Ser | Ile | — | — | — | Leu | Glu | Leu | Val | Trp | Met | Leu | Ser | Ala | His | Ser | Val | Ala |
| | 42 | | | | | | | | | | | | 54 | | | | 165 | | | | | | | | | | | | 175 |
| DyP | Gln | Ala | Pro | Leu | Pro | Thr | Leu | Thr | Gln | His | Thr | Thr | Glu | — | — | — | Val | Ala | Pro | Phe | Thr | Gly | Thr | Thr | Ile | His | Gly | Val | Phe |
| | 33 | | | | | | | | | | | | 45 | | | | 159 | | | | | | | | | | | | 171 |
| TP | Gly | Ala | Ser | Ile | Ile | Leu | Arg | Leu | Phe | Phe | His | Asp | Cys | Phe | — | — | Arg | Asp | Met | Val | Ala | Leu | Ser | Gly | Ala | His | Thr | Ile | Gly |
| | 33 | | | | | | | | | | | | 45 | | | | 161 | | | | | | | | | | | | 173 |
| HAP | Ala | Ala | Ser | Ile | Ile | Arg | Leu | His | Phe | His | Asp | Cys | Phe | — | — | — | Ser | Asp | Leu | Val | Ala | Leu | Ser | Gly | Gly | His | Thr | Phe | Gly |

US 7,041,486 B1

SEQUENCE LISTING

<160> NUMBER OF SEQ ID NOS: 16

<210> SEQ ID NO 1
<211> LENGTH: 6
<212> TYPE: PRT
<213> ORGANISM: Geotrichum candidum

```
<400> SEQUENCE: 1

Thr Tyr Val Pro Glu Arg
1               5

<210> SEQ ID NO 2
<211> LENGTH: 8
<212> TYPE: PRT
<213> ORGANISM: Geotrichum candidum

<400> SEQUENCE: 2

Cys Pro Phe Gly Ala His Val Arg
1               5

<210> SEQ ID NO 3
<211> LENGTH: 21
<212> TYPE: PRT
<213> ORGANISM: Geotrichum candidum

<400> SEQUENCE: 3

Ile Pro Tyr Gly Pro Glu Thr Ser Asp Ala Glu Leu Ala Ser Gly Val
1               5                   10                  15

Thr Ala Gln Asp Arg
            20

<210> SEQ ID NO 4
<211> LENGTH: 21
<212> TYPE: PRT
<213> ORGANISM: Geotrichum candidum

<400> SEQUENCE: 4

Ser Gly Ala Pro Ile Asp Leu Ala Pro Thr Ala Asp Asp Pro Ala Leu
1               5                   10                  15

Gly Ala Asp Pro Gln
            20

<210> SEQ ID NO 5
<211> LENGTH: 6
<212> TYPE: PRT
<213> ORGANISM: Geotrichum candidum

<400> SEQUENCE: 5

Pro Tyr Gly Pro Glu Thr
1               5

<210> SEQ ID NO 6
<211> LENGTH: 6
<212> TYPE: PRT
<213> ORGANISM: Geotrichum candidum

<400> SEQUENCE: 6

Pro Thr Ala Asp Asp Pro
1               5

<210> SEQ ID NO 7
<211> LENGTH: 498
<212> TYPE: PRT
<213> ORGANISM: Geotrichum candidum

<400> SEQUENCE: 7

Met Asp Leu Ser Leu Phe Val Val Ser Val Ala Val Leu Val Gly Ser
1               5                   10                  15

Ser Ser His Val Asn Ala Ala Lys Leu Gly Ala Arg Gln Thr Arg Thr
            20                  25                  30
```

```
Thr Pro Leu Leu Thr Asn Phe Pro Gly Gln Ala Pro Leu Pro Thr Leu
        35                  40                  45

Thr Gln His Thr Thr Glu Ser Gly Ala Asn Asp Thr Ile Leu Pro Leu
    50                  55                  60

Asn Asn Ile Gln Gly Asp Ile Leu Val Gly Met Lys Lys Gln Lys Glu
65                  70                  75                  80

Arg Phe Val Phe Gln Val Asn Asp Ala Thr Ser Phe Lys Thr Ala
                85                  90                  95

Leu Lys Thr Tyr Val Pro Gln Arg Ile Thr Ser Ala Ala Ile Leu Ile
            100                 105                 110

Ser Asp Pro Ser Gln Gln Pro Leu Ala Phe Val Asn Leu Gly Phe Ser
        115                 120                 125

Asn Thr Gly Leu Gln Ala Leu Gly Ile Thr Asp Asp Leu Gly Asp Ala
        130                 135                 140

Gln Phe Pro Asp Gly Gln Phe Ala Asp Ala Ala Asn Leu Gly Asp Asp
145                 150                 155                 160

Leu Ser Gln Trp Val Ala Pro Phe Thr Gly Thr Thr Ile His Gly Val
            165                 170                 175

Phe Leu Ile Gly Ser Asp Gln Asp Phe Leu Asp Gln Phe Thr Asp
            180                 185                 190

Asp Ile Ser Ser Thr Phe Gly Ser Ser Ile Thr Gln Val Gln Ala Leu
        195                 200                 205

Ser Gly Ser Ala Arg Pro Gly Asp Gln Ala Gly His Glu His Phe Gly
        210                 215                 220

Phe Leu Asp Gly Ile Ser Gln Pro Ser Val Thr Gly Trp Glu Thr Thr
225                 230                 235                 240

Val Phe Pro Gly Gln Ala Val Val Pro Pro Gly Ile Ile Leu Thr Gly
            245                 250                 255

Arg Asp Gly Asp Thr Gly Thr Arg Pro Ser Trp Ala Leu Asp Gly Ser
            260                 265                 270

Phe Met Ala Phe Arg His Phe Gln Gln Lys Val Pro Glu Phe Asn Ala
        275                 280                 285

Tyr Thr Leu Ala Asn Ala Ile Pro Ala Asn Ser Ala Gly Asn Leu Thr
        290                 295                 300

Gln Gln Glu Gly Ala Glu Phe Leu Gly Ala Arg Met Phe Gly Arg Trp
305                 310                 315                 320

Lys Ser Gly Ala Pro Ile Asp Leu Ala Pro Thr Ala Asp Asp Pro Ala
            325                 330                 335

Leu Gly Ala Asp Pro Gln Arg Asn Asn Asn Phe Asp Tyr Ser Asp Thr
            340                 345                 350

Leu Thr Asp Glu Thr Arg Cys Pro Phe Gly Ala His Val Arg Lys Thr
        355                 360                 365

Asn Pro Arg Gln Asp Leu Gly Gly Pro Val Asp Thr Phe His Ala Met
        370                 375                 380

Arg Ser Ser Ile Pro Tyr Gly Pro Glu Thr Ser Asp Ala Glu Leu Ala
385                 390                 395                 400

Ser Gly Val Thr Ala Gln Asp Arg Gly Leu Leu Phe Val Glu Tyr Gln
            405                 410                 415

Ser Ile Ile Gly Asn Gly Phe Arg Phe Gln Gln Ile Asn Trp Ala Asn
            420                 425                 430

Asn Ala Asn Phe Pro Phe Ser Lys Pro Ile Thr Pro Gly Ile Glu Pro
        435                 440                 445
```

```
Ile Ile Gly Gln Thr Thr Pro Arg Thr Val Gly Gly Leu Asp Pro Leu
    450                 455                 460
Asn Gln Asn Glu Thr Phe Thr Val Pro Leu Phe Val Ile Pro Lys Gly
465                 470                 475                 480
Gly Glu Tyr Phe Phe Leu Pro Ser Ile Ser Ala Leu Thr Ala Thr Ile
                485                 490                 495
Ala Ala

<210> SEQ ID NO 8
<211> LENGTH: 1494
<212> TYPE: DNA
<213> ORGANISM: Geotrichum candidum

<400> SEQUENCE: 8
atgcgcttgt cgctgtttgt cgtgtcggtt gccgtactcg tcgggtcgag ctcgcatgtc      60
aatgctgcta aactcggcgc gagacagacg cgtacgacac ccctcctcac taattttccg     120
ggacaagccc cgctgccgac tctaacgcag catacgactg agagcggggc caacgataca     180
attctgcccc tgaacaacat acaaggcgac attttggttg gcatgaagaa acagaaggaa     240
cgcttcgtct ttttccaagt caatgacgca acctcgttca agacggcgtt gaagacctac     300
gtgcctgagc gcatcacgtc ggcggcgatt ttgatttcag atccttctca gcagccgttg     360
gctttcgtca acctcgggtt ttcgaacaca ggcctccagg cgcttggaat taccgacgat     420
ctgggtgatg cacaattccc agatggtcag ttcgcagacg ccgcaaacct cgggacgac      480
ctcagccaat gggtggcgcc ttttactggt accaccatcc atggtgtctt tctgattggt     540
aggcgaccag gacgacttct tggatcagtt cacggatgat atctcttcga cctttggttc     600
tccatcactc aggtgcaggc gctcagtggg tctgcgcgtc caggagatca ggctggtcat     660
gaacacttcg ggttcctcga cggcatctcg cagccctcag tcacaggctg ggagacgacc     720
gtcttccctg acaggcggt cgtcccacct ggaattatcc tcactggacg cgatggggac     780
acgggcaccc gaccgtcgtg ggctctagat gggagtttca tggcattccg gcacttccag     840
cagaaggtcc ccgaattcaa cgcgtacacg ctcgccaacg cgatacccgc gaacagcgcg     900
ggaaacctca cccagcagga aggtgcagag ttcctcggcg cgcgcatgtt cggccgttgg     960
aagagcggcg cgccgattga cctcgcgccg acggcggacg acccagcgct cggcgccgac    1020
ccgcagagga caacaatttc gattactca gacacgctga cggacgagac gcgctgcccc    1080
ttcggtgcac acgtgaggaa gacgaaccct cgacaggacc tgggtggacc ggtcgacacc    1140
ttccacgcta tgcggtccag tatcccgtac ggcccagaaa cgtctgatgc agaacttgcg    1200
tcgggcgtga ctgcgcaaga ccgcggtctt cttttcgtcg agtaccagtc cattattggt    1260
aatgggttca ggttccagca gattaactgg gcgaacaatg cgaacttccc tttctccaaa    1320
ccgatcacgc ctggaattga gcctatcatc ggccagacga ctccacgcac tgtcggcggg    1380
ctcgaccccc tcaaccagaa tgagacgttc acagtaccgc tgtttgtgat cccgaagggc    1440
ggggaatact ttttcttgcc ctctatctct gcgctcactg cgactatcgc tgct          1494

<210> SEQ ID NO 9
<211> LENGTH: 26
<212> TYPE: PRT
<213> ORGANISM: Geotrichum candidum
<220> FEATURE:
<221> NAME/KEY: NON_CONS
<222> LOCATION: (13)..(14)

<400> SEQUENCE: 9
```

```
Gln Ala Pro Leu Pro Thr Leu Thr Gln His Thr Thr Glu Val Ala Pro
1               5                   10                  15

Phe Thr Gly Thr Thr Ile His Gly Val Phe
            20                  25
```

<210> SEQ ID NO 10
<211> LENGTH: 26
<212> TYPE: PRT
<213> ORGANISM: Saccharomyces cerevisiae
<220> FEATURE:
<221> NAME/KEY: NON_CONS
<222> LOCATION: (13)..(14)

<400> SEQUENCE: 10

```
Gly Pro Val Leu Val Arg Leu Ala Trp His Thr Ser Gly Arg Glu Val
1               5                   10                  15

Val Ala Leu Met Gly Ala His Ala Leu Gly
            20                  25
```

<210> SEQ ID NO 11
<211> LENGTH: 26
<212> TYPE: PRT
<213> ORGANISM: Escherichia coli
<220> FEATURE:
<221> NAME/KEY: NON_CONS
<222> LOCATION: (13)..(14)

<400> SEQUENCE: 11

```
Ala Gly Leu Phe Ile Arg Met Ala Trp His Gly Ala Gly Glu Thr Val
1               5                   10                  15

Ala Leu Ile Ala Gly Gly His Thr Leu Gly
            20                  25
```

<210> SEQ ID NO 12
<211> LENGTH: 26
<212> TYPE: PRT
<213> ORGANISM: Arthromyces ramosus
<220> FEATURE:
<221> NAME/KEY: NON_CONS
<222> LOCATION: (13)..(14)

<400> SEQUENCE: 12

```
Val Arg Lys Ile Leu Arg Ile Val Phe His Asp Ala Ile Asp Glu Val
1               5                   10                  15

Val Asp Leu Leu Ala Ala His Ser Leu Ala
            20                  25
```

<210> SEQ ID NO 13
<211> LENGTH: 26
<212> TYPE: PRT
<213> ORGANISM: Phanerochaete
<220> FEATURE:
<221> NAME/KEY: NON_CONS
<222> LOCATION: (13)..(14)

<400> SEQUENCE: 13

```
Ala His Glu Val Ile Arg Leu Thr Phe His Asp Ala Ile Phe Glu Val
1               5                   10                  15

Val Ser Leu Leu Ala Ser His Thr Val Ala
            20                  25
```

<210> SEQ ID NO 14
<211> LENGTH: 26
<212> TYPE: PRT

```
<213> ORGANISM: Phanerochaete chrysosporium
<220> FEATURE:
<221> NAME/KEY: NON_CONS
<222> LOCATION: (13)..(14)

<400> SEQUENCE: 14

Ala His Glu Ser Ile Arg Leu Val Phe His Asp Ser Ile Leu Glu Leu
1               5                   10                  15

Val Trp Met Leu Ser Ala His Ser Val Ala
            20                  25

<210> SEQ ID NO 15
<211> LENGTH: 26
<212> TYPE: PRT
<213> ORGANISM: Tunip
<220> FEATURE:
<221> NAME/KEY: NON_CONS
<222> LOCATION: (13)..(14)

<400> SEQUENCE: 15

Gly Ala Ser Ile Leu Arg Leu Phe Phe His Asp Cys Phe Arg Asp Met
1               5                   10                  15

Val Ala Leu Ser Gly Ala His Thr Ile Gly
            20                  25

<210> SEQ ID NO 16
<211> LENGTH: 26
<212> TYPE: PRT
<213> ORGANISM: horse radish
<220> FEATURE:
<221> NAME/KEY: NON_CONS
<222> LOCATION: (13)..(14)

<400> SEQUENCE: 16

Ala Ala Ser Ile Ile Arg Leu His Phe His Asp Cys Phe Ser Asp Leu
1               5                   10                  15

Val Ala Leu Ser Gly Gly His Thr Phe Gly
            20                  25
```

ENZYME HAVING DECOLORIZING ACTIVITY AND METHOD FOR DECOLORIZING DYES BY USING THE SAME

TECHNICAL FIELD

The present invention relates to a novel peroxidase enzyme with high dye degradation activity, the genetic information thereof and a method for degrading and decolorizing dyes by using the same.

BACKGROUND ART

Many of various synthetic dyes discharged from the processes of staining fiber products and from dyestuff production processes are slightly biodegradable substances, involving much difficulty in the degradation thereof in the nature. Because such colored wastewater is hazardous for the nature, regulations over the wastewater have increasingly been tightened.

In the fields of staining industry and dyestuff production industry, wastewater containing dyes has conventionally been treated, mainly by physical or chemical methods such as adsorption, concentration, chemical transformation and incineration. Although these treatment methods are efficient, these methods disadvantageously involve secondary pollution due to the generation of hazardous byproducts and the discharge of the greenhouse effect gas via high-level energy consumption.

Recently, attention has been focused on a treatment method actively utilizing biotechnology with microorganisms or enzymes, as an alternative of the treatment methods. Several microbial strains capable of degrading dyes and colored substances have already been reported. For example, *Phanerochaete chrysosporium* as one species of white rot fungus is listed, which is known as one of lignin-degrading fungus.

However, all the dye-degrading microorganisms known so far have an activity to degrade only one or several types of dyes, so the ability of the microorganisms to treat dyes via degradation is naturally limited. Therefore, the development of an efficient method for treating of wastewater containing dyes has been desired.

Some of the present inventors have isolated a microorganism capable of degrading azo type- and anthraquinone type-dyes, namely *Geotrichum candidum* Dec 1 (which was internationally deposited at the National Institute of Bioscience and Human-Technology, the Ministry of International Trade and Industry, at 1-1-3, Higashi, Tsukuba, Ibaraki, Japan [transferred on Feb. 17, 2000 from the original deposit (FERM P-15348); the accession number was FERM BP-7033] from the nature and have developed a method for degrading and decolorizing a wider range of dyes by microbial treatment (Japanese Patent Laid-open No. 9-173051).

It has been assumed that the excellent ability of *Geotrichum candidum* Dec 1 strain to degrade dyes may possibly be based on the peroxidase activity of the fungal strain, but no instance of specific isolation or identification of such enzyme has been found. Hence, the genetic information thereof has absolutely never been elucidated.

The present invention has been attained toward the industrial demand as mentioned above. An object of the invention is to provide an enzyme applicable to more efficient treatment of wastewater containing dyes and a method for degrading and decolorizing dyes by using the enzyme.

The *Geotrichum candidum* Dec 1 strain exerts an activity to degrade a wide range of dyes and has also prominent enzyme stability. Therefore, the fungal strain per se or after immobilization on an appropriate carrier can be used for degrading dyes.

So as to enhance the industrial applicability, however, the treatment of wastewater containing dyes, particularly dye degradation should essentially be attained in an efficient manner economically.

It is useful for that purpose to use a dye-degrading enzyme owned by said microorganism through isolation and purification rather than to use the microorganism per se, to further elucidate the genetic constitution thereof to realize the mass production of the enzyme and to use them in combination.

The present inventors have made investigations so as to attain the purpose. Because the novel fungus *Geotrichum candidum* Dec 1 strain exerts wide decolorizing spectra over various dyes, the inventors have made further investigations with their attention focused on the dye-degrading enzymes produced by the fungus. The inventors have successfully isolated and identified one of the enzymes, elucidated the gene encoding the enzyme and developed a mass expression system of the enzyme.

DISCLOSURE OF THE INVENTION

The first aspect of the invention is a peroxidase (sometimes abbreviated as DyP hereinafter) derived from *Geotrichum candidum* Dec 1 strain (FERM BP-7033), which has the following properties:
a) a property to degrade and decolorize dyes;
b) a molecular weight of 60 kDa, by the molecular weight assay using SDS-PAGE;
c) a molecular weight of 55 kDa, by the molecular weight assay using gel filtration; and
d) pI (isoelectric point) 3.8, by the assay by isoelectric focusing.

The second aspect of the invention is the enzyme in the first aspect, having the amino acid sequence of SEQ ID NO. 7 in the sequence listing.

The third aspect of the invention is the gene encoding the enzyme in the first aspect, having the DNA sequence of SEQ ID NO. 8 in the sequence listing.

The fourth aspect of the invention is an expression plasmid vector comprising the coding gene in the third aspect.

The fifth aspect of the invention is a microorganism transfected with the expression plasmid vector in the fourth aspect.

The sixth aspect of the invention is a method for degrading and decolorizing dyes, which comprises using the enzyme in the first aspect or the microorganism in the fifth aspect for degrading and decolorizing dyes.

BRIEF DESCRIPTION OF THE DRAWINGS

FIG. 4 shows comparison between the primary structure in the proximity of the arginine (Arg) residue and the histidine (His) residue positioned at the center of the activity. In the figure, open square (□) shows the position of the proximal Arg residue, while open circle (○) shows the position of the proximal His residue and closed circle (●) shows the position of distal His residue.

BEST MODE FOR CARRYING OUT THE INVENTION

Figure 1:
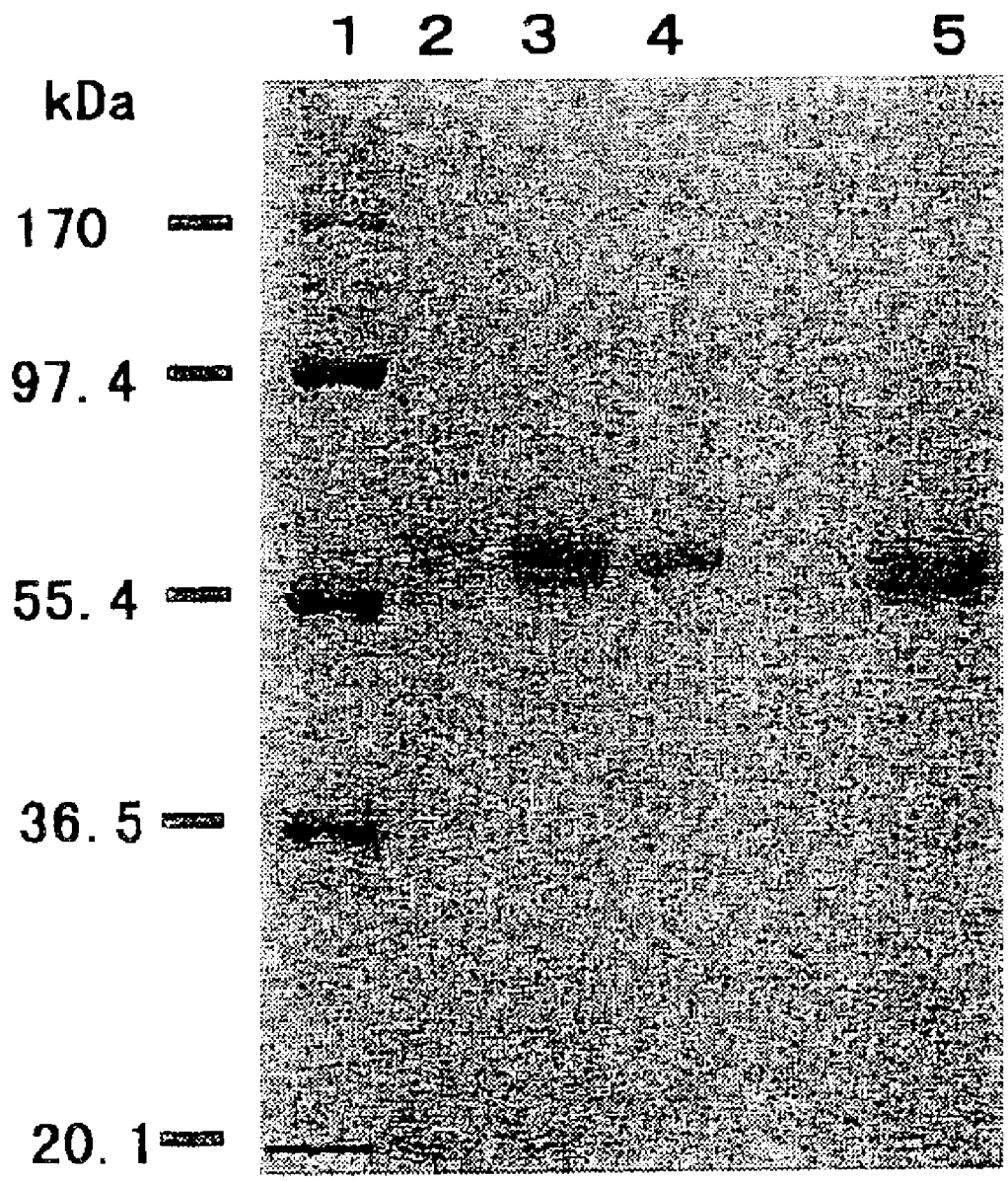
FIG. 1 depicts the results of the SDS electrophoresis of the enzyme DyP of the invention. In the figure, the left numerical figures show molecular weight, while the upper numerical Figures 1 to 5 independently represent the molecular weight marker, crude enzyme solution, the enzyme solution after ion exchange chromatography, the enzyme solution after hydrophobic chromatography and the enzyme solution after ion exchange chromatography, in this order.

The invention is now described in detail hereinbelow.

The peroxidase of the invention is derived from *Geotrichum candidum* Dec 1 strain. The inventors isolated and purified the enzyme as follows.

[Preparation of Culture Broth]

According to general methods, *Geotrichum candidum* Dec 1 strain (FERM BP-7033) was cultured in a liquid culture medium of any composition. Any liquid culture medium of any composition can be used, as long as *Geotrichum candidum* Dec 1 strain can grow in the liquid culture medium. One preferable example is the potato dextrose culture medium (sometimes abbreviated as PD hereinbelow) manufactured by Difco, Co., Ltd. So as to promote the induction of the intended enzyme, further, dyes may be added to the culture medium.

The cultivating conditions of the fungal strain may satisfactorily be determined in light of the type of the culture medium used. When the PD culture medium is selected, for example, the fungal strain is cultured at 15 to 37° C., preferably at 30° C. for 3 to 8 days.

The culture broth thus recovered is subjected as a starting material for the purification of the dye-degrading enzyme to the following steps.

[Purification of Dye-degrading Enzyme]

The dye-degrading enzyme is now to be purified. The purification conditions are not specifically limited. For the purpose of the protection of the enzyme activity against inactivation, the culture broth is preferably handled at a low temperature, particularly in refrigerator.

Specifically, the microorganisms are first separated from the culture broth, from which the supernatant is recovered. In that case, separation processes such as filtration, centrifugation and membrane filtration may satisfactorily be used. Preferably, however, the microorganisms are removed via centrifugation, followed by filtration with glass filter. Contaminating polysaccharides are removed by performing the combination thereof, to recover a crude enzyme solution at a high purity.

Subsequently, the recovered crude enzyme solution may be subjected to isolation, by using the dye-degrading activity described below as a marker. Prior to such isolation, however, concentration and desalting may be carried out so as to readily enable the separation, to prepare a concentrated crude enzyme solution.

Concentration may be done by methods for general use, for example ultra-filtration, salting-out, and evaporation. Preferably, concentration may be carried out by ultra-filtration. Additionally, desalting may be carried out by dialysis, ultra-filtration and electro-dialysis.

From the recovered concentrated crude enzyme solution can then be isolated the intended dye-degrading enzyme, by using the dye-degrading activity as the marker.

As the method therefor, ion exchange resin column chromatography, hydrophobic column chromatography, gel filtration column chromatography and the like may be used.

One of these column chromatography types or a combination of several types thereof may be used, to collect active fractions to isolate and purify the dye-degrading enzyme.

By the procedures, the inventors recovered the intended purified enzyme. The purified enzyme (205-fold active product) is at a single band by SDS-polyacrylamide gel electrophoresis (sometimes abbreviated as SDS-PAGE hereinbelow). The enzyme is the dye-degrading enzyme, peroxidase in the first aspect of the invention. The inventors designated the enzyme DyP.

[Properties of the Purified Dye-degrading Enzyme DyP]

The properties of the inventive enzyme DyP purified by the procedures were measured according to the following principles.

First, the molecular weight was measured by SDS-PAGE and gel filtration chromatography.

For the measurement by SDS-PAGE, a commercially available molecular weight standard kit for electrophoresis may be used as the molecular weight standard.

One example thereof includes Combithek manufactured by Boehringer Mannheim Yamanouchi, Co., Ltd. The kit comprises α-2-macroglobulin (molecular weight of 170 kDa), phosphorylase B (molecular weight of 97.4 kDa), glutamate dehydrogenase (molecular weight of 55.4 kDa), lactate dehydrogenase (molecular weight of 36.5 kDa), and trypsin inhibitor (molecular weight of 20.1 kDa).

As shown in FIG. 1 depicting the results of the measurement, the molecular weight of the inventive enzyme DyP is 60 kDa.

For the assay of the molecular weight of the enzyme by gel filtration chromatography, additionally, the inventors used Sephacryl S-200 column and the standard molecular weight protein (manufactured by BIO-RAD, Co., LTD.).

Consequently, the molecular weight of the inventive enzyme DyP was assayed as 55 kDa.

Then, the isoelectric point of the inventive enzyme was measured. The isoelectric point was measured by isoelectric focusing.

Figure 2:
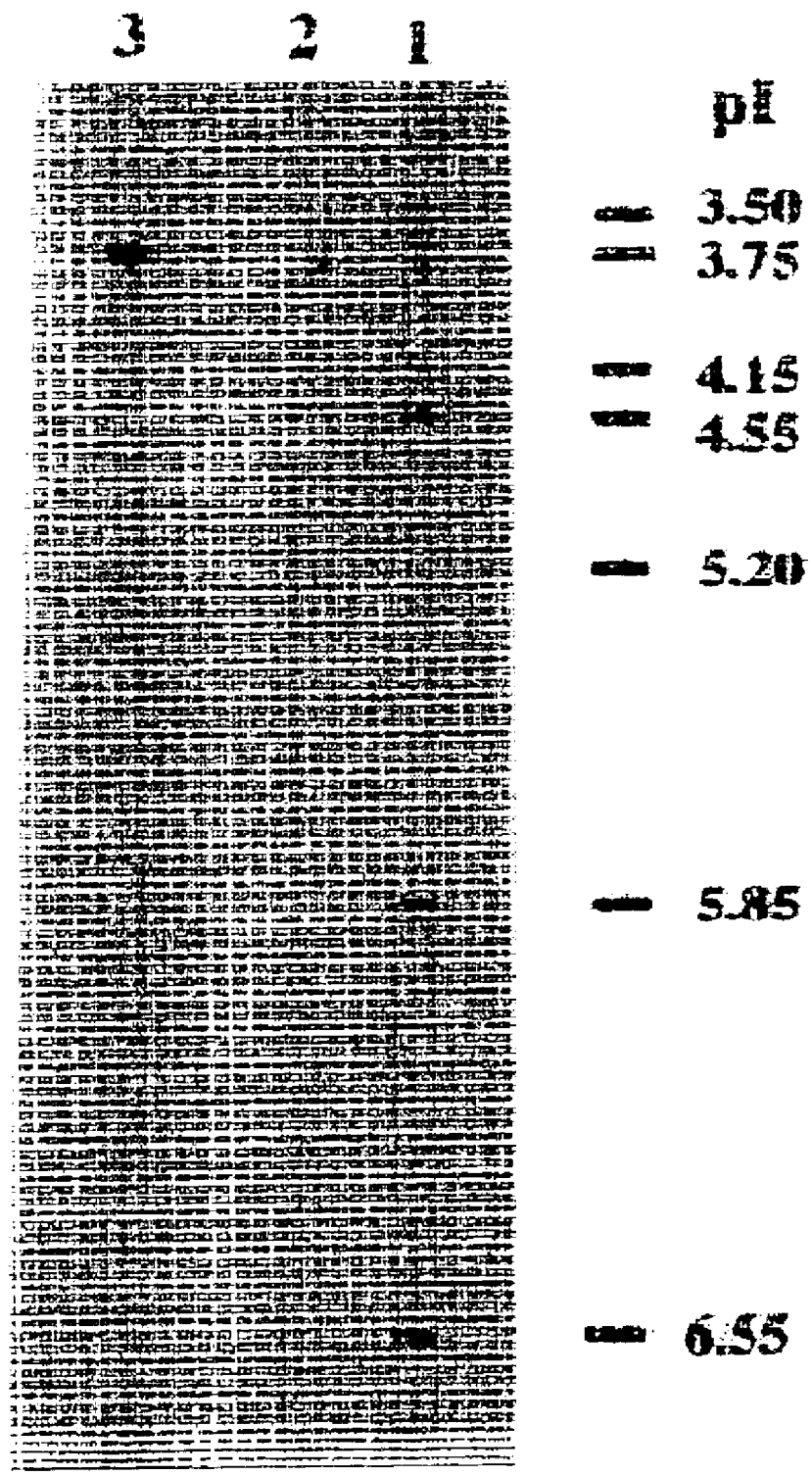
FIG. 2 depicts the results of the isoelectric focusing of the enzyme DyP of the invention. In the figure, the right numerical figures show isoelectric points (pI), while the upper numerical Figures 1 to 3 independently represent crude enzyme solution, purified DyP and the isoelectric point marker, in this order.

Consequently, the isoelectric point of the enzyme DyP was assayed as pI=3.8, as shown in FIG. 2.

[Dye-degrading Spectrum of Dye-degrading Enzyme DyP]

The dye-degrading enzyme DyP of the invention has an enzyme activity over azo type- and anthraquinone type-dyes, in particular, among dyes, and has an ability to degrade and decolorize these pigments.

The anthraquinone type dyes include for example Reactive blue 5, Reactive blue 19 and Reactive blue 114 (all manufactured by Nippon Kayaku Co., Ltd.); 1-amino-4-(3-amino-4-sodium-sulfonoanilino)-2-sodium anthraquinone sulfonate (sometimes abbreviated as AQ-1 hereinafter) and 1-amino-4-methylamino-2-sodium-anthraquinone sulfonate (sometimes abbreviated as AQ-2 hereinafter).

Herein, Reactive blue 5 is the compound represented by the following chemical formula.

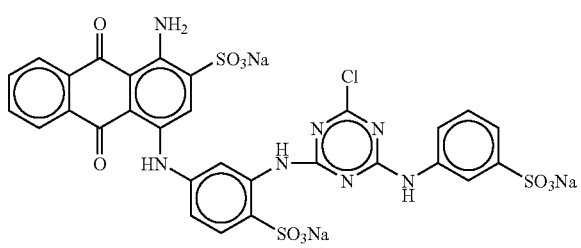

AQ-1 is the compound represented by the following chemical formula.

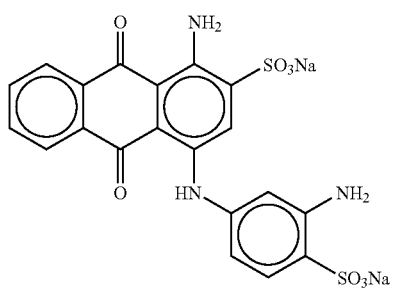

AQ-2 is the compound represented by the following

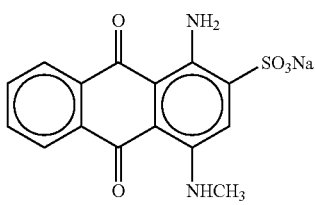

Further, the azo type dyes include for example Reactive black 5, Reactive red 33, Reactive yellow 2 and Reactive blue 182 (all manufactured by Nippon Kayaku Co., Ltd.).

Other than the dyes, the dye-degrading enzyme DyP has an ability to degrade phenolic compounds such as 2,6-dimethoxyphenol and guaiacol, which are known as substrates for manganese peroxidase (sometimes abbreviated as MnP hereinafter). As shown in the following examples, however, no effect of manganese compounds added to the reaction solution on the promotion of the enzyme activity is observed.

Alternatively, no reaction of DyP with veratryl alcohol known as a substrate of lignin peroxidase (sometimes abbreviated as LiP hereinafter) is observed.

As described above, surprisingly, DyP exerts substrate specificity different from those of MnP and LiP known so far. Thus, DyP can be said as a peroxidase differing from the known enzymes.

[Optimum Reaction Temperature of Dye-degrading Enzyme DyP]

Figure 3:
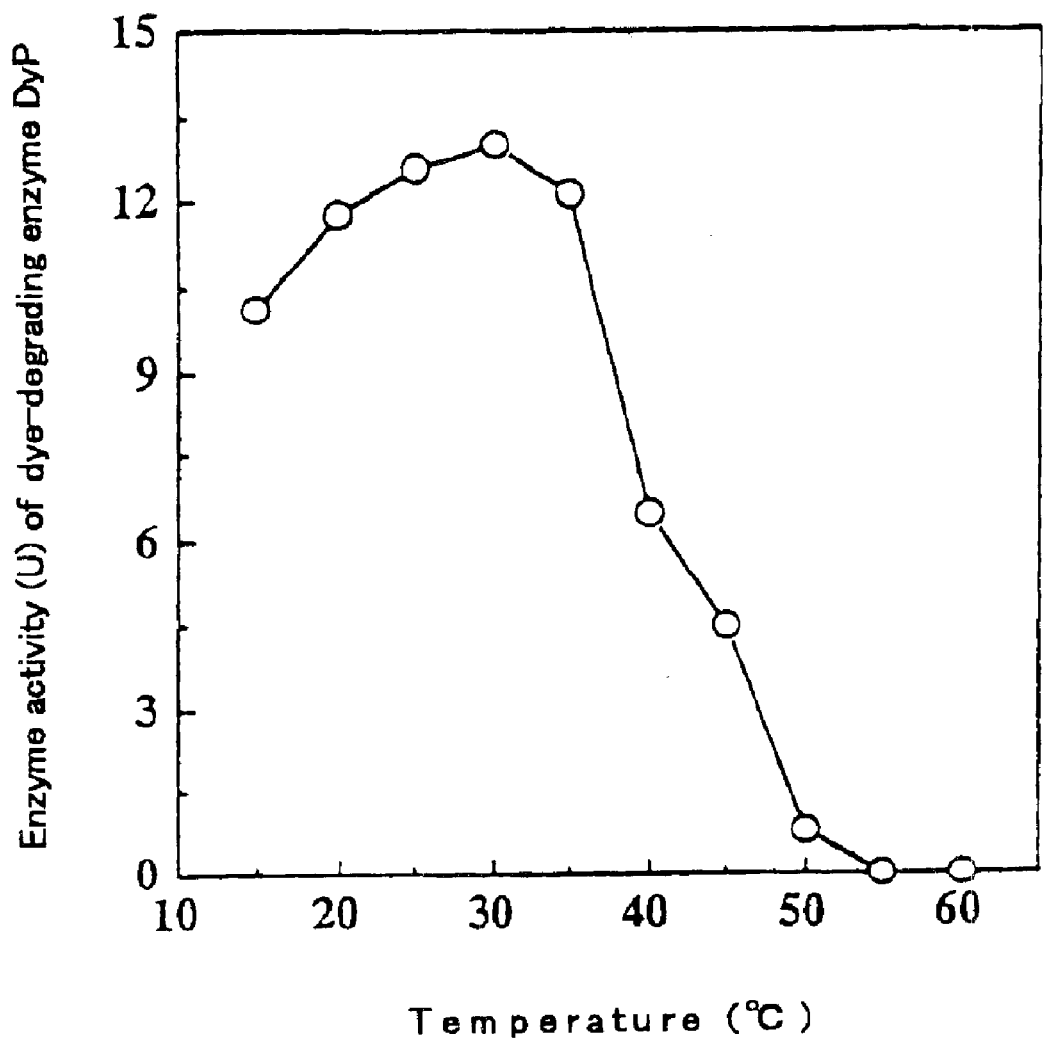
FIG. 3 is a graph depicting the relation between the enzyme activity of the inventive enzyme DyP and temperature.

The optimum reaction temperature of the inventive dye-degrading enzyme DyP is around 30° C., as shown in FIG. 3. The enzyme DyP exerts stable dye-degrading activity within a temperature range of 15° C. to 35° C. However, the enzyme activity rapidly decreases at a temperature above 35° C.

[Temperature Stability of Dye-degrading Enzyme DyP]

After the inventive dye-degrading enzyme DyP was stored at a fixed temperature for a fixed period of time, the ratio of the remaining activity was subsequently evaluated.

Specifically, a solution of the dye-degrading enzyme DyP in 25 mM citrate buffer was stored at 30° C. or 40° C. for 14 days.

Consequently, the remaining enzyme activity of DyP was at 63% when DyP was stored at 30° C.; and the activity was at 41% when DyP was stored at 40° C.

So as to compare the temperature stability with those of other peroxidases, solutions of individual enzymes in 25 mM citrate buffer were stored at 60° C. for 3 hours, by using a commercially available horse-radish peroxidase (manufactured by Wako Chemical Co., Ltd.; sometimes abbreviated as HRP hereinafter) as the control. Subsequently, the remaining enzyme activities were compared to each other.

Consequently, it was shown that 65% of the activity of the inventive dye-degrading enzyme DyP remained, but only 10% of the activity of HRP remained.

The results show that the dye-degrading enzyme DyP has greater thermal stability, compared with currently known peroxidases.

The enzyme characteristics of the novel dye-degrading enzyme DyP in accordance with the invention are described hereinabove.

The dye-degrading enzyme DyP of the invention exerts a wider range of dye-degrading activity, compared with any of currently reported dye-degrading enzymes, and has also prominent enzyme stability, as apparently shown in the enzyme characteristics.

In the sixth aspect of the invention, hence, the use of the dye-degrading enzyme DyP enables efficient degradation and decolorization of such dyes.

So as to raise the industrial applicability of the dye-degrading enzyme DyP, essentially, efficient degradation of wastewater containing dyes and dyes should be attained economically.

One example includes a method using DyP after immobilization. The method comprises immobilizing DyP through adsorption or covalent bonding on immobilization carriers, such as ion exchange resin, synthetic polymer gel, naturally originated active charcoal and zeolite, and using the resulting DyP as bioreactor. For creating highly active bioreactor, the method is more useful than the method using the microorganism per se after immobilization.

As a means for more economically producing the enzyme, the gene encoding the intended enzyme is isolated, which is then introduced in a host microorganism capable of expressing the enzyme at a mass scale, so that DyP at a higher purity can be recovered more efficiently in a more stable manner.

Compared with the case of using the microorganism per se, a combination thereof enables the preparation of a bioreactor with a far more excellent cost performance.

[Schema of Isolation of Gene Encoding Dye-degrading Enzyme DyP]

From the above respects, the inventors carried out the following procedures so as to obtain the genetic information of the DyP of the invention.

The concrete method for isolating the gene is schematically described below.

First, partial hydrolysis of the inventive dye-degrading enzyme DyP purified by the aforementioned method was carried out by allowing trypsin (manufactured by Wako Chemical Co., Ltd.) to react with the enzyme.

The resulting five types of the partially hydrolyzed fragments were purified. Thereafter the amino acid sequences of the individual fragments were determined, to synthetically prepare the coding gene corresponding to each of the amino acid sequences.

Subsequently, PCR-amplified gene was recovered by PCR using the resulting coding gene as a primer and the cDNA derived from *Geotrichum candidum* as a template.

The resulting amplified gene was labeled by using the DIG labeling detection kit (manufactured by Boehringer Mannheim, Co., Ltd.).

By general methods using the labeled amplified gene as a probe, plaque hybridization with the *Geotrichum candidum* Dec 1-derived cDNA library prepared by using lambda phage λgt10, was performed.

From some hybridized colonies thus recovered were cut out the intended genes, which were then integrated into pUC18 plasmid, for subsequent sequencing. This was used as template for the following PCR.

[Determination of Partial Amino Acid Sequence of Dye-degrading Enzyme DyP]

So as to prepare a primer for the gene encoding DyP, DyP was purified.

Purification of DyP can be performed by usual methods. The methods include for example a purification method comprising electroblotting from SDS-PAGE gel and a purification method by high-performance liquid chromatography (HPLC).

After the purified DyP was denatured by ordinary methods, partial hydrolysis thereof using trypsin was performed. Partially digested peptides thus formed were fractionated by HPLC. Consequently, five fragments were recovered. The amino acid sequence of each of the fragments was determined by the Edman method with a protein sequencer. Among the amino acid sequences of the resulting five fragments, the first sequence was Trp Lys. The amino acid sequences of the second and thereafter are shown in the sequence listing, where the second is shown in SEQ ID NO. 1; the third is shown in SEQ ID NO. 2; the fourth is shown in SEQ ID NO. 3 and the fifth is shown in SEQ ID NO. 4.

Among these amino acid sequences, a partial sequence (SEQ ID NO. 5) of SEQ ID NO. 3 and a partial sequence (SEQ ID NO. 6) of SEQ ID NO. 4 were selected as PCR primers.

[Probe Preparation]

DNA encoding the two types of amino acid sequences was synthetically prepared by the following method.

By PCR using the resulting primer genes and the cDNA derived from *Geotrichum candidum* Dec 1 as PCR template, a first-stage gene amplification was practiced. Consequently, new 200-bp primers corresponding to the two primers were recovered.

Both the termini of the primers were subjected to T4 DNA polymerase treatment, to synthetically prepare plasmid-ligation sites. Then, the primers were ligated to the HincII site of pUC 18 as *E. coli* expression vector, to recover a recombinant plasmid.

The recombinant plasmid was amplified, by using *E. coli* JM 109 strain. From the resulting plasmid was cutout the coding gene. By a second PCR, the resulting DNA was sequenced (see the positions 1012 to 1181 of SEQ ID NO. 8 sequence listing).

[Cloning of Gene DyP Encoding Dye-degrading Enzyme DyP]

From the *Geotrichum candidum* Dec 1 strain cultured separately was prepared RNA according to usual methods. From the resulting RNA was purified poly(A)+RNA. Subsequently, the recovered poly(A)+RNA was used to prepare cDNA with a cDNA kit (manufactured by TaKaRa).

After the recovered cDNA was subjected to ligation with T4 polynucleotide kinase kit, DNA of 1,200 to 2,000 bp was fractionated by electrophoresis.

Further, the DNA was inserted in the EcoRI site of lambda phage λgt10, for packaging into the λ phage. The recovered phage was used for infection of *E. coli*.

Colonies hybridizing with the labeled probe previously prepared were screened. As a result, 11 candidates were obtained.

The results of the measurement described above indicate that DyP of the invention has a molecular weight of 60 kDa at a sugar chain content of 17%, so the primary amino acid sequence is estimated to be 49.8 kDa. Additionally, the open reading frame of the gene encoding DyP is estimated to comprise 460 amino acids, namely 1380 bp.

Independently using the coding genes of the recovered 11 candidates, PCR was carried out again to evaluate the fragment size of the inserted cDNA. In other words, genes in the proximity of 1380 bp were screened.

Consequently, clone 92 carrying the cDNA of a 1600-bp size was recovered. The cDNA was cut out with BamHI from the recombinant plasmid, which was then integrated in pUC18. The resulting plasmid was designated pB92. It was verified that the clone 92 had a dye-degrading activity based on the dye-degrading enzyme DyP.

[DNA Sequence of pB92 Gene]

pB92 was sequenced with DNA sequencer. Consequently, it was found that the open reading frame of pB92 comprised 498 amino acids, namely 1494 bp and had a molecular weight of 53,306.

This indicates that pB92 carries the DyP gene. The amino acid sequence of DyP and the nucleotide sequence of the DyP gene, carried in pB92, are shown as SEQ ID NOS. 7 and 8, respectively. In other words, DyP having the amino acid sequence described as SEQ ID NO. 7 in the sequence listing is the enzyme described in the second aspect of the invention, while the gene having the nucleotide sequence described as SEQ ID NO. 8 in the sequence listing is the gene in the third aspect of the invention.

Herein, the gene in the third aspect of invention (see SEQ ID NO. 8 in the sequence listing) when modified with deletion, substitution, addition and the like in a part of the sequence is also encompassed within the scope of the invention, as long as the resulting modified gene has the same effects as those of the gene of the invention.

Further, pB92 as the plasmid vector carrying these genes is described in the fourth aspect of the invention.

Still further, a transformant recovered by transfecting *E. coli* with pB92 is described in the fifth aspect of the invention. When the transformant is used, the dye-degrading enzyme DyP of the invention can efficiently be produced.

The invention will now be described more specifically in examples hereinbelow. However, the invention is not limited to the examples.

EXAMPLE 1

Purification and Properties of Dye-degrading Enzyme DyP

[Purification of Dye-degrading Enzyme DyP]

150 mL of a PD culture medium (potato-dextrose culture medium, manufactured by Difco, Co., Ltd.) was placed in a 500-mL Erlenmeyer flask, into which 5 ml of the spore suspension of *Geotrichum candidum* Dec 1 (FERM BP-7033) strain was inoculated. Then, culturing was started. Culturing was continued at 30° C. and 120 rpm for 6 days.

After culturing, the culture broth was cooled to 4° C. and centrifuged at 7,200×g for 20 minutes. 4,380 mL of the resulting supernatant was used for the following procedures.

The supernatant was filtered through a glass filter (GC50, manufactured by Toyo Roshi Co., Ltd.), to remove the polysaccharide contained therein.

Then, the filtrate was subjected to ultrafiltration on an ultrafiltration membrane (YM10) manufactured by Amicon, Co., Ltd., to concentrate the filtrate to 60 mL. The concentrate was dialyzed against 25 mM piperazine buffer (pH 5.5) and was then concentrated to 17.2 mL, by using Centriprep10 manufactured by Amicon, Co., Ltd.

The concentrate of 17.2 mL was charged on Super Q 650 M column of 2.8×6.0 cm (manufactured by Tosoh Co., Ltd.), which was preliminarily equilibrated with 25 mM piperazine buffer (pH 5.5). Subsequently, the column was rinsed with 200 mL of the same buffer, followed by elution on a linear gradient of 0 to 0.4 M.

Fractions with dye-degrading activity were collected and concentrated to 2.8 mL, by using Centriprep10 manufactured by Amicon, Co., Ltd. The concentrate was charged on Butyl Toyopearl of 1.6×6.5 cm (manufactured by Tosoh Co., Ltd.), which was preliminarily equilibrated with 25 mM citrate buffer (pH 5.5) and 0.8 M ammonium sulfate. Subsequently, the column was rinsed with 50 mL of the same buffer, followed by elution on a linear gradient of ammonium sulfate from 0.8 M to 0, to collect a fraction with the dye-degrading activity, which was defined DyP.

DyP was dialyzed against 25 mM citrate buffer, to recover purified DyP at 1.5 mg. The purified DyP solution was stored at 4° C.

[Properties of Dye-degrading Enzyme]

The molecular weight and isoelectric point of the dye-degrading enzyme DyP recovered by the above procedures were measured.

The molecular weight was determined by SDS-PAGE electrophoresis and gel filtration method.

For SDS-PAGE electrophoresis, 10% polyacrylamide gel and an electrophoresis apparatus of AE-6440 manufactured by Atto Co., Ltd. were used. As the molecular weight control, further, Combithek manufactured by Boehringer Mannheim Yamanouchi, Co., Ltd. was used.

Consequently, the molecular weight of DyP was assayed as 60 kDa.

For gel filtration, alternatively, Sephacryl S-200 column of 3.1×95 cm after equilibration with 25 mM citrate buffer (pH 5.0) was used, together with the standard protein kit manufactured by BIO-RAD Co., Ltd.

Consequently, the molecular weight of DyP was assayed as 55 kDa.

For measurement of isoelectric focusing, a low-pI calibration kit of Multiphor II 2-D for pH 2.5 to pH 6.5, manufactured by Pharmacia, Co. was used. Consequently, the isoelectric point of DyP was assayed as 3.8.

[Assay of Dye-degrading Activity]

The dye-degrading spectrum of the purified DyP was examined for nine types of dyes and three model compounds. The activity of the purified DyP to degrade these dyes or model compounds was assayed by measuring the degradation rates.

As the dyes, use was made of Reactive blue 5, 19 and 114; AQ-1 and AQ-2; Reactive black 5, Reactive red 33, Reactive yellow 2, and Reactive blue 182.

As the model compounds, additionally, use was made of 2,6-dimethoxyphenol, guaiacol and veratryl alcohol.

The dye-degrading activity was measured as follows.

0.2 to 0.4 mM aqueous hydrogen peroxide was added to a mixture solution of 3 mL of 25 mM citrate buffer (adjusted to the optimum pH for the degradation of each of the dyes) containing each dye at a fixed pH (30 to 120 ppm) and 1 mL of 1.86 nM DyP solution, to initiate the enzyme reaction. Reaction was performed at 30° C. for a fixed period of time, to assay the reaction rate.

1 U of the dye-degrading activity was defined as the activity to decolorize 1 μmole Reactive blue 5 or AQ-2 for one minute. The results are shown in Table 1.

TABLE 1

(DyP activity to degrade each dye and model compound)

| Color index | Chromogen | λmax | Optimum pH | Initial concentration (ppm) | Decolorizing activity (ppm/min) |
|---|---|---|---|---|---|
| Reactive blue 5 | AQ | 600 | 3.2 | 100 | 19.8 |
| Reactive blue 19 | AQ | 590 | 3.2 | 70 | 13.1 |
| Reactive blue 114 | AQ | 620 | 4.0 | 100 | 7.8 |
| AQ-1 | AQ | 600 | 3.2 | 60 | 5.4 |
| AQ-2 | AQ | 635 | 3.0 | 50 | 19.5 |
| Reactive black 5 | AZ | 598 | 3.2 | 30 | 0.1 |
| Reactive red 33 | AZ | 500 | 3.2 | 50 | 0.4 |
| Reactive yellow 2 | AZ | 390 | 3.2 | 100 | 0.5 |
| Reactive blue 182 | AZ | 610 | 4.0 | 120 | 20.9 |

As to 2,6-dimethoxyphenol used as a model compound, alternatively, absorbance at 470 nm was calorimetrically measured, which emerged via oxidation.

That is to say, a mixture solution of 2.79 nM DyP and 0.2 mM 2,6-dimethoxyphenol was reacted with 25 mM citrate buffer (pH 4.5) containing 0.2 mM hydrogen peroxide.

As to guaiacol, 1 mM guaiacol was used in place of 0.2 mM 2,6-dimethoxyphenol, for absorbance measurement at 465 nm.

The results about the model compounds are shown in Table 2.

TABLE 2

(DyP activity to degrade model compounds)

| Compound | Group | pH | Initial concentration (mM) | Oxidation rate (ΔOD/min) |
|---|---|---|---|---|
| 2,6-Dimethoxyphenol | phenolic | 4.5 | 0.2 | 0.29 |
| Guaiacol | phenolic | 4.0 | 1.0 | 0.29 |
| Veratryl alcohol | nonphenolic | — | 0.5 | ND |

The results in Table 1 indicate those described below.

The dye-degrading enzyme DyP exerts a high activity to degrade the anthraquinone type pigments. Specifically, the enzyme exerts an excellent degradation activity over Reactive blue 5, Reactive blue 19 and AQ-2, so the enzyme can efficiently degrade these pigments.

Additionally, the enzyme exerts an activity to degrade the azo type pigments. The enzyme efficiently degraded Reactive blue 182, in particular. The enzyme has an ability to degrade other azo type pigments, Reactive black 5, Reactive red 33 and Reactive yellow 2.

This apparently demonstrates that DyP has an action to degrade anthraquinone type pigments and azo type pigments.

Alternatively, the DyP activity over the model compounds is as follows, on the basis of the results in Table 2.

First, 2,6-dimethoxyphenol and guaiacol having phenolic hydroxyl group could efficiently be degraded by DyP. Alternatively, DyP could never degrade veratryl alcohol known as a substrate of lignin peroxidase.

This apparently indicates that DyP has a specifically high enzyme activity over the compounds having phenolic hydroxyl group.

[Optimum Temperature of Dye-degrading Enzyme DyP]

The optimum temperature of DyP was determined by examining the decolorizing (degrading) activity of Reactive blue 5 at a fixed temperature. The results are shown in FIG. 3.

FIG. 3 indicates that DyP exerts a high peroxidase activity within a range of 20 to 35° C., and also indicates that the optimum temperature is 30° C.

EXAMPLE 2

Effect of Metal Ion on the Activity of Dye-degrading Enzyme DyP

Each 5 mM ions of calcium, zinc, copper (divalent), potassium, iron (divalent) and sodium were concurrently present in a reaction solution comprising DyP and 100 ppm Reactive blue 5, so as to examine the effects of these metal ions on the relative activity of the DyP enzyme.

The results are shown in Table 3.

TABLE 3

(Influence of metallic cation on DyP activity to degrade dyestuff)

| Metal ion | Concentration (mM) | Specific activity (%) |
|---|---|---|
| No addition | — | 100 |
| $Ca^{++}$ | 5 | 81 |
| $Zn^{++}$ | 5 | 69 |
| $Cu^{++}$ | 5 | 75 |
| $K^+$ | 5 | 81 |
| $Na^+$ | 5 | 81 |
| $Fe^{++}$ | 0.2 | 50 |

Table 3 shows that the enzyme exhibited a relative activity of about 80%, when the ions were added, compared with the case of no addition. Particularly, the divalent iron ion concurrently present at 0.2 mM inhibited the activity at 50%.

This indicates that the concurrent presence of the metal ions affects adversely the enzyme activity of DyP.

EXAMPLE 3

Determination of Gene Encoding DyP and the Amino Acid Sequence Thereof

[Determination of Partial Amino Acid Sequence of Dye-degrading Enzyme DyP]

According to the Laemmli method (Laemmli, U.K. Nature (London), 227, 680–685 (1970)), *Geotrichum candidum* Dec 1 strain (FERM BP-7033) was subjected to SDS-PAGE, to separate purified DyP.

Subsequently, the DyP was electroblotted on polyvinyl difluoride (sometimes abbreviated as PVDF hereinafter) membrane according to the Towbin method (Towbin, H., Staehelin, T., and Gordon, J. Proc. Natl. Acad. Sci. USA, 76, 4350–4354 (1979)).

The PVDF membrane was treated with Coomassie Brilliant Blue (CBB-250), from which was then cut out solely the membrane corresponding to the stained band portion of the DyP. The band was then transferred in a 1.5-mL test tube. 50 μL methanol was added to the test tube, followed by addition of 200 μL reductive buffer (buffer, pH 8.5, containing 8 M guanidine hydrochloride salt, 0.5 M Tris buffer, 0.3% ethylendiaminetetraacetate disodium (EDTA-2Na) and 5% acetonitrile), for gradual shaking, from which the reductive buffer was removed.

Then, 50 μL reductive buffer containing 1 mg dithiothreitol was added onto the protein on the PVDF membrane, which was then left at 25° C. for one hour. After the PVDF membrane was transferred in a 200-mL conical beaker, followed by sequential rinsing individually with 100 mL water for 5 minutes, 100 mL 2% acetonitrile for 5 minutes and 100 mL 0.1% SDS for 5 minutes.

Thereafter, the PVDF membrane was transferred into a fresh 1.5-mL test tube, followed by addition of 500 μL polyvinylpyrrolidone PVP-40 (sometimes abbreviated as PVP-40 hereinafter) containing 1 mg methionine according to the Iwamatsu method (Iwamatsu, A. Electrophoresis, 13, 142–147 (1992)), and the resulting mixture was left to stand at ambient temperature for 30 minutes.

After the PVDF membrane was additionally rinsed with 100 mL 10% acetonitrile solution, it was rinsed three times with 500 μL of degradation buffer (100 mM ammonium bicarbonate, 10 mM calcium chloride, pH 7.8). Then the rinse solutions were discarded. Continuously, 500 μL of the same degradation buffer except for the content of 1 pmol trypsin was added, and then enzymatic reaction was carried out at 25° C. for 12 hours.

After the oligopeptide eluted from the PVDF membrane into the reaction solution was freeze-dried, the freeze-dried oligopeptide was then dissolved in 100 μL degradation buffer, followed by elution on a 0–50% linear gradient (100 minutes, 0.8 mL/min) of isopropyl alcohol-acetonitrile (7:3 v/v) containing 0.02% trifluoroacetic acid by HPLC (column: Capcell-Pak C-18, 4.6×150 mm), to fractionate individual fractions.

The partially degraded peptides fractionated and purified were determined of their primary structures with a protein sequence system (Shimadzu, PPSQ-21).

[Preparation of cDNA Library]

For the purpose of RNA extraction, the culture broth of *Geotrichum candidum* Dec 1 strain was subjected to centrifugation, to separate 25 mL of hypha of the strain. This was placed in a centrifuge tube, followed by addition of liquid nitrogen to freeze the hypha, and then it was freeze-dried for 12 hours to recover a powder.

Over the resulting powder of the hypha was again poured liquid nitrogen, to pulverize the hypha, to which was then added 10 mL of a guanidium solution (containing 4 M guanidium isothiocyanate, 20 mM sodium acetate, pH 5.2, 0.1 mM DTT and 0.5% N-lauroylsarcosine), for homogenization. This was then centrifuged (1,500×g) to obtain the supernatant.

The resulting RNA was separated by cesium chloride ultra-centrifugation method (Ullrich), followed by fractionation of poly(A)⁺RNA using oligo (dT) cellulose column. The resulting poly(A)⁺RNA was used to synthetically prepare cDNA with a cDNA synthesis kit (TaKaRa; Gulbler-Hoffman).

Into the resulting cDNA was inserted an adaptor (EcoRI-NotI-BamHI), by using a DNA ligation kit. Both the ligated termini were phosphorylated with T4 polynucleotide kinase, to separate cDNA by agarose electrophoresis.

Further, 1200- to 2000-bp cDNA corresponding to the molecular weight of DyP was separated among the resulting cDNAs, to which was then added 8 μL of TE buffer (10 mM Tris-HCl, pH 8.0, 1 mM EDTA-2Na) to elute the cDNA.

The recovered cDNA fragment was ligated in the EcoRI site of λ phage. This was packaged into λ phage with Gigapack Gold Packaging Extract (Stratagene, La Jolla Calif., USA).

After *E. coli* NM514 strain was infected with lambda phage λgt 10 at 37° C. for 15 minutes, the infected strain was overlaid on LB agar medium (bacto-tryptone, 0.5% bacto-yeast extract, 1% sodium chloride, 1.5% agar/1,000 mL), by using 0.7% agar. The plate was cultured at 37° C. for 12 hours.

[Sequencing of Coding Gene of Dye-degrading Enzyme DyP]

Colonies hybridizing with the preliminarily prepared labeled probe were screened. That is to say, by plaque hybridization of the colonies, 11 candidates were consequently selected from the positive cDNA library and DNAs recovered by PCR.

These were ligated with pUC18 plasmid via T4 DNA ligase, for amplification in *E. coli* JM109 strain.

Because DyP has a molecular weight of 60 kDa at a sugar chain content of 17%, on the basis of the results of the measurement of the DyP properties, the primary amino acid sequence is estimated to be of 49.8 kDa. Additionally, it is estimated that the open reading frame of the DyP coding gene will comprise 460 amino acids, namely 1380 bp.

Then, the coding genes of the resulting 11 candidates were used for PCR again. Among the inserted cDNAs, a gene around 1380 bp was screened.

Consequently, clone 92 carrying the cDNA of a 1600-bp size was obtained.

By using BamHI, the cDNA was cleaved out of the recombinant plasmid, which was then inserted in pUC18. The resulting plasmid was designated pB92.

Subsequently, the plasmid DNA was prepared by the alkali extraction method. Both the resulting strands were analyzed and sequenced by a DNA sequencer (Model 4000L, Li-Cor Inc., Lincoln, Neb., USA).

[Expression in a Host of Different Species]

The open reading frame of the pB92 thus recovered comprises 1494 bp, namely 498 amino acids (see SEQ ID NO. 7 in the sequence listing). Thus, the molecular weight estimated from the number of the amino acids was 53,306. This indicates that the pB92 carries the DyP gene.

Furthermore, pB92 was transformed into *E. coli*. The transformant (*Escherichia coli* JM109/pYES92) was deposited at the National Institute of Bioscience and Human-technology, the Ministry of International Trade and Industry, 1-1-3, Higashi, Tsukuba, Ibaraki, Japan on Feb. 16, 2000. The accession number was FERM BP-7032. The transformant was cultured in L culture medium (0.5% yeast extract, 0.5% NaCl, 1.0% tryptone), and harvested and disrupted, to confirm the DyP activity.

[Comparison with Other Peroxidase Sequences]

Homology screening of the DyP gene (SEQ ID NO. 9) was carried out, by using three types of databases (Genebank, EMBL, DDBJ). Consequently, the peroxidase derived from U77073 (*Polyporaceae* sp.) registered at the Genebank, was screened, which was a gene homologous with DyP. Then, the homology between the two was examined. When regions with high homology were examined, the region at position 407 to position 438 was at the highest homology of 88%, while the region at position 62 to position 85 was 83% homologous. For the whole sequence of the gene, only 56% homology was observed. Additionally, peroxidases with high homology, except for the peroxidase derived from *Polyporaceae* sp., were never found.

[Comparison with Other Peroxidases Derived from Fungi]

Microbial peroxidase is classified in plant-type peroxidase. Plant-type peroxidases are systematically classified into three classes by Welinder et al. (Welinder, Curr. Opin. Struct. Biol., 2, 388–393 (1992)). According to the classification, peroxidases from prokaryote organisms or eukaryote mitochondria are classified in Class I, while fungal peroxidases are classified in Class II and higher plant-derived peroxidases are classified in Class III.

The classification by Welinder et al. is based on the comparison of highly common sequences in the primary sequence of each peroxidase. In more detail, the classification is practiced by comparing the primary sequences around the His residue proximal to the heme iron and the His residue distal to the heme iron and the Arg residue. Using the sequence comparison table prepared by Welinder et al., the DyP sequence was compared (FIG. 4). Herein, FIG. 4 includes CCP (*Saccharomyces cerevisiae*-derived cytochrome C peroxidase) and ECP (*E. coli*-derived peroxidase) as Class I peroxidases. Comparison was done with ARP (*Arthromyces ramosus*-derived peroxidase), MnP (manganic peroxidase derived from a fungus of the genus *Phanerochaete*) and LiP (*Phanerochaete chrysosporium*-derived lignin peroxidase) as Class II peroxidases. Additionally, Class III peroxidase includes TP (Tunip peroxidase) and HRP (horse radish peroxidase).

Because DyP is derived from the fungus, DyP is classified in Class II. However, it was shown that the Arg residue (at the open square (□) position in the figure) characteristically found in Class II was absent and no homology was found with the sequence in the proximity of the distal His residue (at dosed circle (●) position in the figure). This indicates that DyP as a fungus-derived peroxidase has a specific sequence.

INDUSTRIAL APPLICABILITY

In accordance with the invention, the peroxidase with high degradation activity of a wide range of dye types as well as the method for degrading the dye types by using the enzyme can be provided. Additionally, the invention provides the genetic information of the enzyme and can supply the enzyme at a large scale on the basis of the information. Thus, the enzyme can be applied to the treatment of wastewater containing dyes and the like, in the fields of staining industry and the like.

Accordingly, the immobilization of the enzyme as a dye-degrading enzyme can raise the industrial applicability thereof as a bioreactor with higher activity.

What is claimed is:

1. An isolated polynucleotide having the nucleic acid sequence of SEQ ID NO. 8.

2. An expression plasmid vector comprising the polynucleotide of claim 1.

3. An *Escherichia coli* JM109/pYES92 FERM BP-7032 transformed with the expression plasmid vector of claim 2.

4. A method for degrading and decolorizing a dye, comprising contacting said dye with a bacterium expressing a peroxidase enzyme encoded by the plasmid contained in *Escherichia coli* JM109/pYES92 FERM BP-7032 wherein said dye is selected from the group consisting of an azo-containing dye, an anthraquinone-containing dye, and a phenolic compound; wherein said phenolic compound is selected from the group consisting of 2,6-dimethoxyphenol and guaiacol.

5. The method according to claim 4, wherein the dye is an azo-containing or anthraquinone-containing dye.

6. The method according to claim 4, wherein the dye is at least one member selected from the group consisting of Reactive black 5, Reactive red 33, Reactive yellow 2, Reactive blue 182, Reactive blue 19, Reactive blue 5, Reactive blue 114, 1-amino-4-(3-amino-4-sodium-sulfonoanilino)-2-sodium anthraquinone sulfonate, and 1-amino-4-methylamino-2-sodium-anthraquinone sulfonate.

7. The method according to claim 4, wherein the dye is at least one phenolic compound selected from the group consisting of 2,6-dimethoxyphenol and guaiacol.

8. The method according to claim 4, wherein the contacting is performed at temperature ranging from 15 to 35° C.

9. The method according to claim 4, wherein the enzyme is immobilized.

* * * * *